US007901924B2

(12) United States Patent
San et al.

(10) Patent No.: US 7,901,924 B2
(45) Date of Patent: Mar. 8, 2011

(54) INCREASED BACTERIAL COA AND ACETYL-COA POOLS

(75) Inventors: Ka-Yiu San, Houston, TX (US); George Nelson Bennett, Houston, TX (US); Ravishankar V. Vadali, Indianapolis, IN (US)

(73) Assignee: Rice University, Houston, TX (US)

( * ) Notice: Subject to any disclaimer, the term of this patent is extended or adjusted under 35 U.S.C. 154(b) by 10 days.

(21) Appl. No.: 12/340,349

(22) Filed: Dec. 19, 2008

(65) Prior Publication Data

US 2009/0186398 A1 Jul. 23, 2009

Related U.S. Application Data

(63) Continuation of application No. 10/808,717, filed on Mar. 24, 2004, now abandoned.

(60) Provisional application No. 60/457,093, filed on Mar. 24, 2003, provisional application No. 60/457,635, filed on Mar. 26, 2003.

(51) Int. Cl.
| | |
|---|---|
| *C12N 1/20* | (2006.01) |
| *C12N 15/74* | (2006.01) |
| *C12N 9/04* | (2006.01) |
| *C12N 9/10* | (2006.01) |
| *C12N 9/12* | (2006.01) |
| *C12N 15/00* | (2006.01) |
| *C12P 21/06* | (2006.01) |
| *C12P 19/34* | (2006.01) |

(52) U.S. Cl. ............... 435/252.3; 435/252.8; 435/471; 435/190; 435/193; 435/194; 435/69.1; 435/91.1; 435/320.1

(58) Field of Classification Search ............ 435/252.3, 435/252.8, 471, 190, 193, 194, 69.1, 91.1, 435/320.1
See application file for complete search history.

(56) References Cited

U.S. PATENT DOCUMENTS 4,766,071 A 8/1988 Simon et al.

OTHER PUBLICATIONS

Stephens et al., The pyruvate dehydrogenase complex of *Escherichia coli* K12 nucleotide sequence encoding the dihydrolipoamide acetyltransferase component. Eur. J. Biochem., 1983, vol. 133: 481-489.*
Yang et al., The effects of feed and intracellular pyruvate levels on the redistribution of metabolic fluxes in *Escherichia coli*. Metabolic Eng., 2001, vol. 3: 115-123.*
Broun et al., Catalytic plasticity of fatty acid modification enzymes underlying chemical diversity of plant lipids. Science, 1998, vol. 282: 1315-1317.*
Calder et al., Cloning and characterization of a eukaryotic pantothenate kinase gene (panK) from *Aspergillus nidulans*. J. Biol. Chem., 1999, vol. 274 (4): 2014-2020.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol.,2001, vol. 183 (8): 2405-2410.*
Song et al., Cloning, sequencing, and expression of the pantothenate kinase (coaA) gene of *Escherichia coli*. 1992, vol. 174 (20): 6411-6417.*
Stephens et al., The pyruvate dehydrogenase complex of *Escherichia coli* K12. Eur. J. Biochem., 1983, vol. 133: 155-162.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Yun et al., Sructural basis for the feedback regulation of *Escherichia coli* pantothenate kinase by coenzyme A. J. Biol. Chem., 2000, vol. 275 (36): 28093-28099.*
San et al., Metabolic Engineering through Cofactor Manipulation and Its Effects on Metabolic Flux Redistribution in *Escherichia coli*, Metabolic Engineering 4, 182-192 (2002).
Lin H, Vadali RV, Bennett GN, San KY. Increasing the Acetyl-CoA Pool in the Presence of Overexpressed Phosphoenolpyruvate Carboxylase or Pyruvate Carboxylase Enhances Succinate Production in *Escherichia coli*. Biotechnol. Prog. Sep.-Oct. 2004;20(5):1599-604.
San KY, Bennett GN, Berrios-Rivera SJ, Vadali RV, Yang YT, Horton E, Rudolph FB, Sariyar B, Blackwood K. Metabolic Engineering Through Cofactor Manipulation and its Effects on Metabolic Flux Redistribution in *Escherichia coli*. Metab. Eng. Apr. 2002;4(2):182-92.
Vadali R.V., Bennett GN, San KY. Cofactor Engineering of Intracellular CoA/acetyl-CoA and its Effect on Metabolic Flux Redistribution in *Escherichia coli*. Metab. Eng. Apr. 2004;6(2):133-9.
Vadali R.V., Bennett GN, San KY. Enhanced Moamyl Acetate Production Upon Manipulation of the Acetyl-CoA Node in *Escherichia coli*. Biotechnol Prog. May-Jun. 2004;20(3):692-7.
Vadali R.V.; Bennett, G. N.; San, K.-Y. ApplicMability of CoA/acetyl-CoA Manipulation System to Enhance Isoamyl Acetate Production in *Escherichia coli*. Metabolic Engineering. 2004a, 6, 294-299.
Rock C.O. et al., Pantothenate Kinase Regulation of the Intracellular Concentration of Coenzyme A, J. Biol. Chem. 2000, 275, 1377-1383.
Mason A. B, Alcohol Acetyltransferase and the Significance of Ester Synthesis in Yeast , Yeast, 2000, 16, 1287-1298.
Vallari D. et al., Biosynthesis and Degadation Both Contribute to the Regulation of Coenzyme A Content in *Escherichia coli*, J. Bacteriol. Sep. 1988, 17, 3961-3966.
Voet D. et al., Biochemistry, second edition, 1995, John Wiley & Sons, Inc., pp. 543-548.
Yang et al., Effect of Inactivation of nuo and ackA-pta on Redistribution of Metabolic Fluxes in *Escherichia coli*, Biotec. Bioeng. 1999, 65, 291-297.
Mansi El-Mansi et al., Control of Carbon Flux Through Enzymes of Central and Intermediary Metabolism During Growth of *Escherichia coli* on Acetate, Current Option in Microbiol. 2006, 9, 173-179.

(Continued)

*Primary Examiner* — Ganapathirama Raghu
(74) *Attorney, Agent, or Firm* — Boulware & Valoir

(57) ABSTRACT

Methods of increasing the cellular pool of A-CoA and thus driving the metabolic pathways in the direction of A-CoA containing metabolites by overexpressing rate limiting enzymes in A-CoA synthesis. Methods of increasing intracellular levels of CoA and A-CoA through genetic engineering of bacterial strains in conjunction with supplementation with precursor molecules.

9 Claims, 11 Drawing Sheets

OTHER PUBLICATIONS

Song W. J. et al., Cloning, Sequencing, and Expression of the Pantothenate Kinase (coaA) Gene of *E. coli*, J. Bacteriol. 1992, 6411-6417.

Russell G.C. et al., Overproduction of the Pyruvate Dehydrogenase Multicomplex of *Escherichia coli* and Site-Directed Substitutions in the E1p and E2p Subunits, Biochem. J. 1992, 287, 611-619.

Examples of ethyl esters, The Alchemist Web page printout, Mar. 18, 2008.

Brown, T.D.K., et al., The enzymic interconversion of acetate and acetyl-coenzyme A in *Escherichia coli*. Journal of General Microbiology 102:327-336 (1977).

* cited by examiner

SEQUENCE LISTING

```
<160> NUMBER OF SEQ ID NOS: 2

<210> SEQ ID NO 1
<211> LENGTH: 36
<212> TYPE: DNA
<213> ORGANISM: Artificial
<220> FEATURE:
<223> OTHER INFORMATION: primer

<400> SEQUENCE: 1
cccaagcttt gtggatggag ttaagtcagt agaaag                              36

<210> SEQ ID NO 2
<211> LENGTH: 29
<212> TYPE: DNA
<213> ORGANISM: Artificial
<220> FEATURE:
<223> OTHER INFORMATION: primer

<400> SEQUENCE: 2
ccatcgattt aaagcgacgc aaattcgcc                                     29
```

INCREASED BACTERIAL COA AND ACETYL-COA POOLS

PRIOR RELATED APPLICATIONS

This application is a continuation of Ser. No. 10/808,717, filed on Mar. 24, 2004, which claims the benefit of U.S. Provisional Application No. 60/457,093, filed Mar. 24, 2003 and U.S. Provisional Application No. 60/457,635, filed Mar. 26, 2003.

FEDERALLY SPONSORED RESEARCH STATEMENT

The present invention may have been developed with government funds. Therefore, the United States Government and the National Science Foundation, under Grant Nos. BES-0118815 and 0000303, may have certain rights in the invention.

REFERENCE TO MICROFICHE APPENDIX

A Sequence Listing, including SEQ ID NO: 1 and 2, is submitted with this application.

FIELD OF THE INVENTION

The invention relates to methods of increasing intracellular levels or flux of CoA and A-CoA through genetic engineering of bacterial strains in conjunction with supplementation with precursor molecules. The invention further relates to methods of increasing the cellular pool or flux of A-CoA and thus driving the metabolic pathways in the direction of A-CoA containing metabolites and A-CoA derivatives.

BACKGROUND OF THE INVENTION

Coenzyme A (CoA) and its thioester derivative Acetyl CoA (A-CoA) are essential intermediates in numerous biosynthetic and energy yielding metabolic pathways as well as regulators of several key metabolic reactions. A-CoA is an important intracellular metabolite in central carbon metabolism and is a precursor in the enzymatic synthesis of many useful compounds. A-CoA is formed during the enzymatic oxidation of pyruvate or fatty acids, and from free acetate in the presence of the enzyme acetyl-CoA synthase. There are several key rate limiting steps in the biosynthesis of A-CoA. The overexpression of the enzymes catalyzing these rate limiting steps increases the intracellular levels of A-CoA. The A-CoA node serves as a connecting point at which several metabolic pathways intersect. Enhancing the A-CoA flux, i.e., the amount of A-CoA generated in a given time, through the A-CoA node is a useful strategy for increasing the production of compounds that require A-CoA for their biosynthesis.

CoA and A-CoA are precursors to many industrially useful compounds. A-CoA is also a substrates in alcohol acetyl transferase reactions that produce various acetate esters. In addition, A-CoA and its condensation product acetoacetyl-CoA are involved in the biological production of various polyhydroxybutyrates (PHBs). A-CoA can be carboxylated to malonyl-CoA and subsequently enter pathways to isoprenoid and terpenoid compounds through mevalonate. In sum, enhancing the intracellular pools/flux of A-CoA has implications in improving the production of the useful compounds derived from A-CoA.

Existing methodologies focus on the engineering of metabolic pathways by overexpressing enzymes that are directly involved in the production of a target compound. The invention claimed and described herein differs from existing methodologies in that in the present invention, cellular metabolism is altered to increase glycolytic flux and to direct this increased flux towards the production of precursor molecules such as A-CoA. The increased production of A-CoA in turn increases the production of target compounds such as esters, PHBs and polyketides.

Metabolic engineering has the potential to considerably improve process productivity by manipulating the throughput of metabolic pathways. Most current metabolic engineering studies focus on manipulating enzyme levels through the amplification, addition, or deletion of a particular pathway. However, cofactors play an essential role in a large number of biochemical reactions and their manipulation has the potential to be used, as an additional tool to achieve desired metabolic engineering goals. In addition, cofactor manipulation may also provide an additional means to study cellular metabolism, in particular the interplay between cofactor levels/fluxes and metabolic fluxes.

SUMMARY OF THE INVENTION

An aspect of the invention provides a method for increasing the levels of CoA or A-CoA in an *E. coli* strain through the genetic manipulation of the strain. Another aspect of the invention provides a microorganism with increased intracellular levels of CoA or A-CoA.

An aspect of the invention provides a method for manipulating the metabolism of a cell, comprising expression at elevated levels of one or more enzymes involved in A-CoA metabolism, wherein the cell displays increased flux through the A-CoA node.

A further aspect of the invention provides a microorganism which expresses one or more enzymes involved in A-CoA metabolism at elevated levels, wherein said microorganism displays increased flux through the A-CoA node.

An aspect of the invention provides a method of producing isoamyl acetate in a cell comprising expression at elevated levels of one or more enzymes involved in A-CoA metabolism, wherein the cell displays increased flux through the A-CoA node

BRIEF DESCRIPTION OF THE DRAWINGS

The accompanying drawings which are incorporated in and constitute a part of this specification exemplify the invention and together with the description, serve to explain the principles of the invention.

DESCRIPTION OF EXEMPLARY EMBODIMENTS

Reference will now be made in detail to embodiments of the invention, examples of which are illustrated in the accompanying drawings.

An application of this invention can be to increase the production of esters, PHBs and polyketides. Coenzyme A (CoA) and A-CoA are precursors to fatty acid biosynthesis. Hence with the manipulation of CoA and A-CoA, fatty acid biosynthesis can potentially be altered.

Esters are an important class of chemical compounds used in food and flavor industries. Certain of the useful compounds derived from an increase in the levels of CoA and A-CoA include, but are not limited to, succinate, isoamyl alcohol and isoamyl acetate. Esters such as isoamyl acetate may be used in nail polish, lacquer coatings, plasticizers and other industrial applications.

Figure 1:
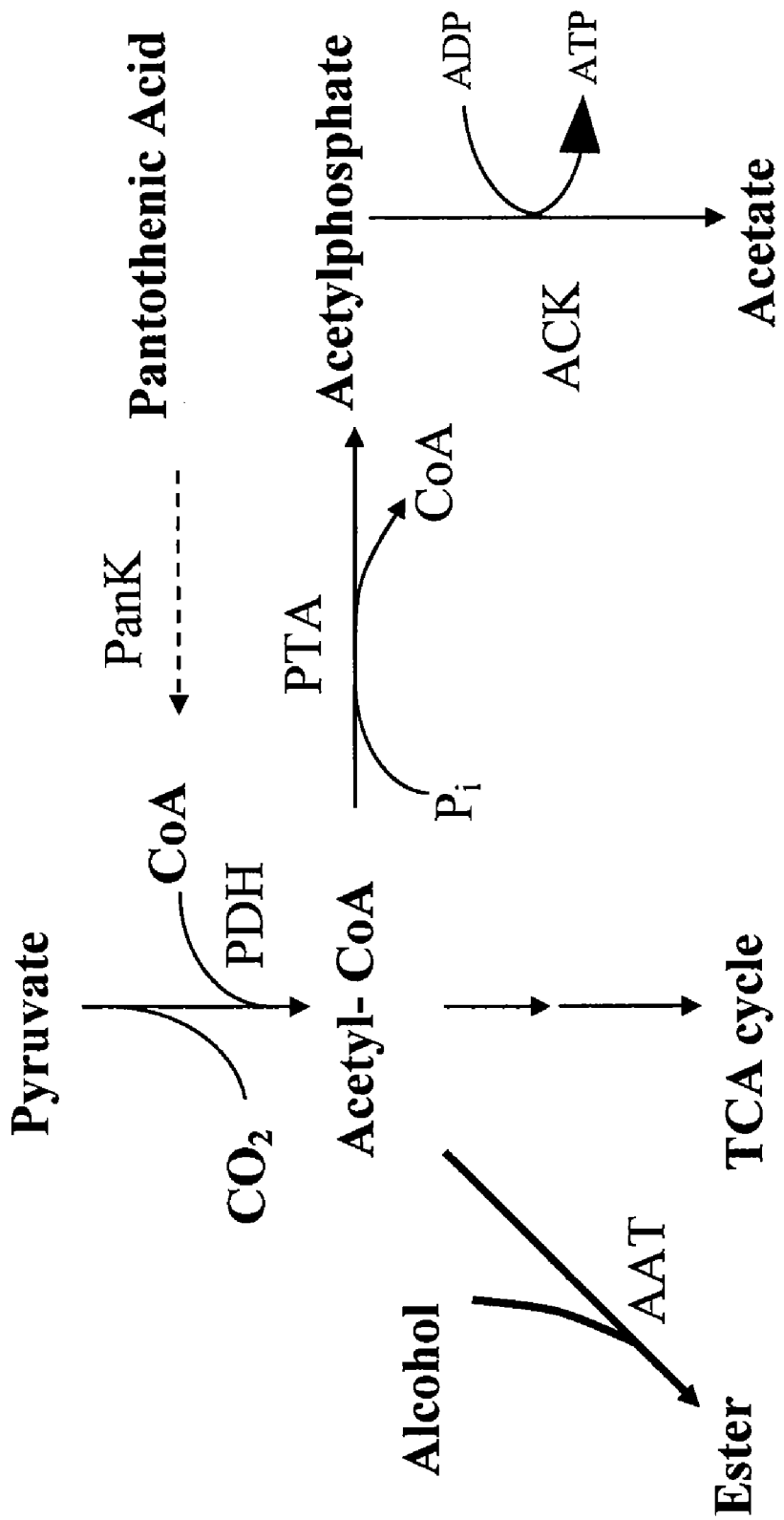
FIG. 1 illustrates the metabolic pathway at the A-CoA node.

FIG. 1 shows the intersection of metabolic pathways at the A-CoA node. Pyruvate is oxidatively decarboxylated to A-CoA by pyruvate dehydrogenase (PDH), which subsequently enters the tricarboxylic acid (TCA) cycle. In the presence of an alcohol, A-CoA may be converted to an ester using an alcohol acetyltransferase (AAT). In the presence of inorganic phosphate (Pi), A-CoA may be converted to acetyl phosphate by phosphotransacetylase (PTA), which in turn may be converted to acetate using acetate kinase (ACK).

Figure 2:
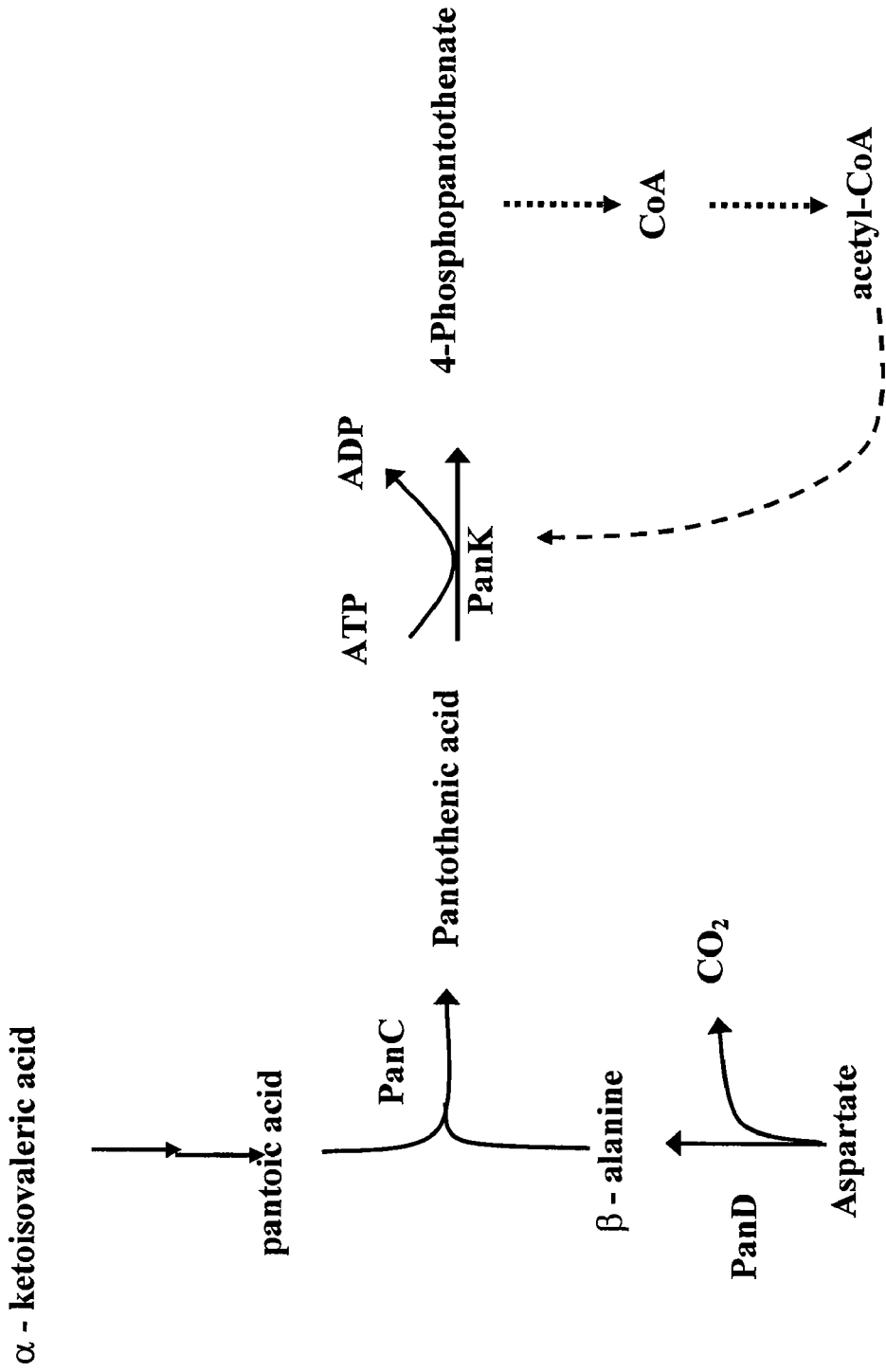
FIG. 2 illustrates the involvement of pantothenate kinase in the biosynthesis of CoA.

FIG. 2 shows the involvement of pantothenate kinase (PanK) in the CoA biosynthetic pathway. Also shown is the negative regulation of PanK by CoA and acetyl CoA.

In general, the invention relies on the introduction of one or more genes into a microorganism, which in turn result in increased intracellular levels of CoA and/or A-CoA.

In an embodiment of the invention, an isolated recombinant construct comprising the gene encoding PanK is introduced into an *E. coli* strain.

In an alternate embodiment of the invention, an isolated recombinant construct comprising the gene encoding pyruvate dehydrogenase (PDH) is introduced into an *E. coli* strain together with an isolated recombinant construct comprising the gene encoding PanK.

In an embodiment of the invention, an *E. coli* strain is transformed with an isolated recombinant construct comprising the gene encoding PanK, where the panK gene is under the control of the lac promoter and additionally comprising the ATF2 (Alcohol Acetyltransferase 2) gene under the control of the ptb (Phosphotransbutyrylase) promoter.

In general, the invention relies on the introduction of one or more genes into a microorganism, where the genes encode enzymes that catalyze one or more rate limiting steps of A-CoA biosynthesis. An example of an enzyme involved in a rate limiting step of A-CoA synthesis is pantothenate kinase. Overexpression of the gene encoding pantothenate kinase along with simultaneous supplementation of precursor pantothenic acid, significantly increases intracellular CoA levels (FIG. 1).

Another example of an enzyme involved in a rate limiting step of A-CoA synthesis is pyruvate dehydrogenase. Overexpression of pyruvate dehydrogenase in the presence of elevated levels of pantothenate kinase along with simultaneous supplementation of precursor pantothenic acid, leads to the increased carbon flux from pyruvate to A-CoA.

A third example of an enzyme involved in a rate limiting step of A-CoA synthesis is pyruvate oxidoreductase. Overexpression of pyruvate oxidoreductase in the presence of elevated levels of pantothenate kinase along with simultaneous supplementation of precursor pantothenic acid, leads to the increased carbon flux from pyruvate to A-CoA.

The inventive system and methods described herein may be used to manipulate the production of A-CoA through the overexpression of any active enzyme that is capable of increasing the carbon flux through the A-CoA node.

An embodiment of the invention provides a method of increasing the intracellular pool of A-CoA by elevated expression of at least one gene which encodes an enzyme involved in A-CoA biosynthesis.

As used herein, the enzymes involved in A-CoA metabolism includes all enzymes whose elevated expression results in an increase in the carbon flux through the A-CoA node. These enzymes include enzymes that mediate the conversion of pyruvate to A-CoA, as well as enzymes that catalyze one or more rate-limiting steps of the A-CoA biosynthesis pathway. These enzymes include, but are not limited to, pyruvate dehydrogenase, pyruvate formate lyase, pyruvate oxidoreductase, pantothenate kinase, and mixtures thereof.

Another important enzyme that plays a role in the biosynthesis of CoA is phosphopantetheine adenylytransferase (CoAD). In an embodiment of the invention, overexpression of CoAD leads to the increased carbon flux through the A-CoA node.

In other embodiments of the inventions, the A-CoA level is enhanced through the deletion of an A-CoA utilizing pathway. An alternate embodiment of the invention shows an enhancement of A-CoA levels through the reduction of A-CoA flux through one or more A-CoA utilizing pathways. Examples of such A-CoA utilizing pathways include, but are not limited to, acetate formation pathway of acetate kinase and phosphotransacetylase, the TCA cycle entry of citrate synthase (citrate synthase formation), the fatty acid biosynthesis pathway, the formation of malonyl-CoA (malonate formation), and the condensation of acetyl-CoA via a thiolase (acetoacetate or acetoacetyl CoA formation). These strategies for reduction of utilization of A-CoA can be used in combination with the strategies to increase acetyl-CoA to yield additional incremental increases that are useful in directing metabolism in particular types of cells. Additional ways to increase the level of A-CoA directly through the enzymes that uptake acetic acid such as A-CoA synthetase or other acyl-CoA synthetases that uptake other acids (e.g., propionic acid or butyric acid) could be used in combination with the above-listed strategies.

Example 1

Plasmid Construction

Plasmid pGS367 (Pyruvate dehydrogenase expression plasmid) was obtained from Dr J. R. Guest of Dept of Molecular Biology and Biotechnology, University of Sheffield, Sheffield, UK. Plasmid pSJ380 bearing the panK (Pantothenate Kinase) gene cloned in pET-15b (NOVAGEN™) vector under the control of T7 promoter was obtained from Dr. Suzanne Jackowski of Biochemistry Dept, St Jude Children's Research Hospital, Memphis, Tenn. A 1.5 kb XbaI-BamHI fragment containing the panK gene was cloned into the high copy number plasmid pUC19 to yield the construct pRV380, following which it was cloned into the plasmid pDHK29 using the same restriction sites to yield the construct pRV480. The construct, pRV480, bearing the panK gene is compatible with pGS367. The ATF2 (Alcohol Transferase 2) gene along with the ptb (Phosphotransbutyrylase) promoter was amplified by PCR the construct pTAAT (which carries the ATF2 gene of yeast) as template DNA. The forward and reverse primers used were as follows:

```
                                              SEQ ID NO: 1
5'-CCCAAGCTTTGTGGATGGAGTTAAGTCAGTAGAAAG-3'
(forward primer)

SEQ ID NO: 2
5'-CCATCGATTTAAAGCGACGCAAATTCGCC-3'
(reverse primer)
```

Figure 3:
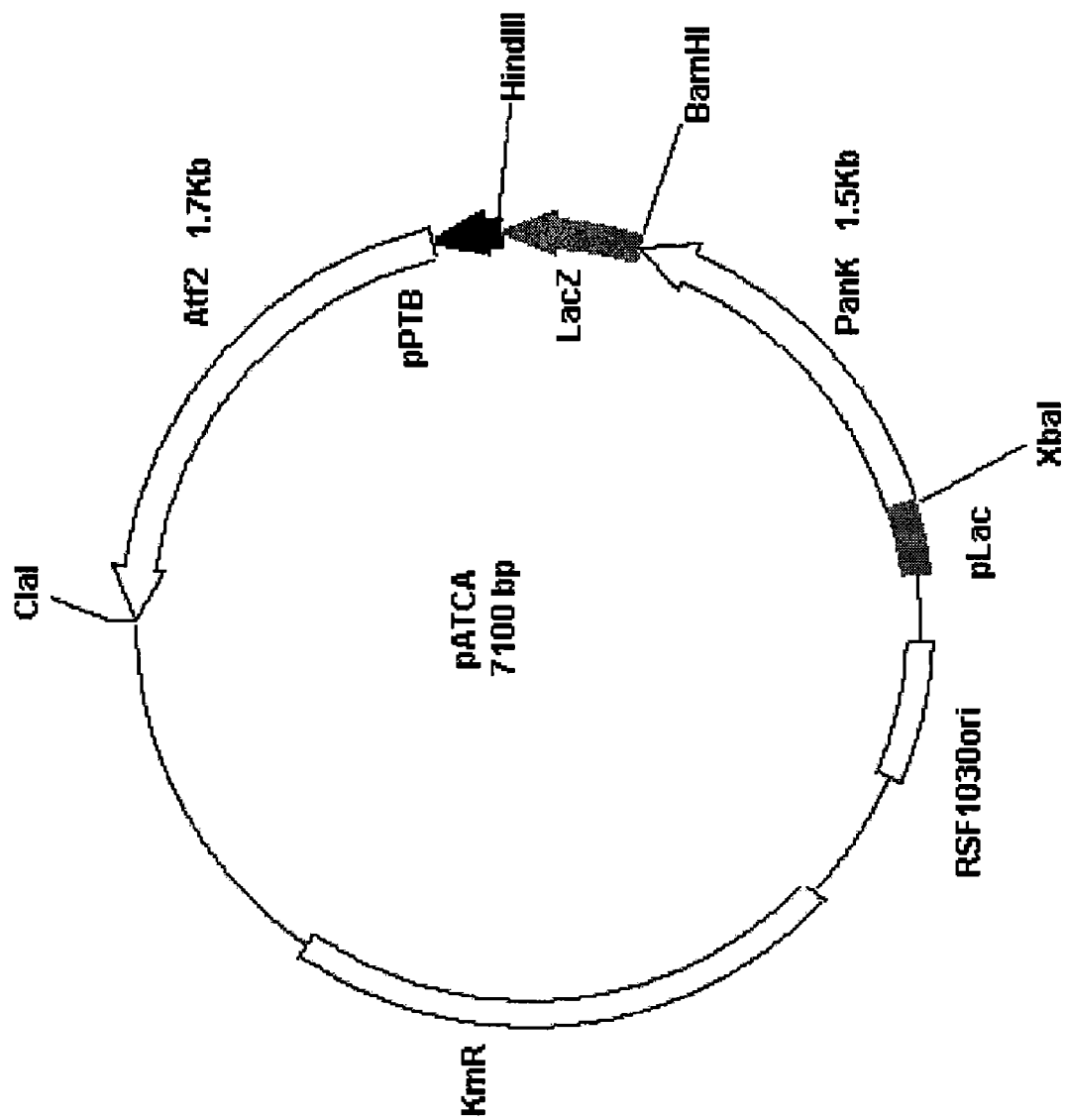
FIG. 3 illustrates a plasmid construct used for the overexpression of pantothenate kinase.

The forward and reverse primers contain HindIII and ClaI restriction sites respectively, which allowed the amplified PCR fragment to be cloned into the corresponding restriction sites of the plasmid pRV480 to yield pATCA (FIG. 3). The newly created pATCA construct contains panK gene under the control of the lac promoter and ATF2 gene under the control of the ptb promoter. This newly constructed plasmid pATCA, bearing the genes panK and ATF2 is compatible with pGS367.

Relevant plasmid constructs were transformed into DH10B or YBS121 bacterial strain to carry out certain exemplary embodiments of the invention.

The plasmids used in certain embodiments of the invention are set forth in Table 1 below. The transformed bacterial strains used in certain embodiments of the invention are set forth in Table 2 below.

TABLE 1

| Plasmid | Properties |
|---|---|
| pGS367 | Pyruvate dehydrogenase expression plasmid |
| pRV480 | Pantothenate kinase expression plasmid |
| pATCA | Pantothenate kinase expression plasmid where the panK gene is under the control of the lac promoter and additionally containing the ATF2 gene under the control of the ptb promoter |
| ptac-85 | IPTG-inducible bacterial expression vector |

TABLE 2

| Recombinant Strain | ATCC Deposit No. | Properties |
|---|---|---|
| DH10B(ptac-85, pRV480) | | Overexpresses pantothenate kinase |
| DH10B(pGS367, pRV480) | | Overexpresses pantothenate kinase and pyruvate dehydrogenase |
| DH10B(ptac-85, pATCA) | | Overexpresses pantothenate kinase expression plasmid where the panK gene is under the control of the lac promoter and additionally containing the ATF2 gene under the control of the ptb promoter |
| DH10B(pGS367, pATCA) | | Overexpresses pantothenate kinase expression plasmid where the panK gene is under the control of the lac promoter and additionally containing the ATF2 gene under the control of the ptb promoter, and pyruvate dehydrogenase |
| YBS121 (pATCA, ptac-85) | | Overexpresses pantothenate kinase expression plasmid where the panK gene is under the control of the lac promoter and additionally containing the ATF2 gene under the control of the ptb promoter |
| YBS121 (pATCA, pGS367) | | Overexpresses pantothenate kinase expression plasmid where the panK gene is under the control of the lac promoter and additionally containing the ATF2 gene under the control of the ptb promoter, and pyruvate dehydrogenase |
| DH10B(pUC19) | | Control |
| DH10B(pRV380) | | Overexpresses panK |
| DH10B(pKmAT, pUC19) | | Control |
| DH10B(pKmAT, pRV380) | | Overexpresses panK |

Example 2

Bioreactor Experiments

Bioreactor studies were performed in a 1 liter (l) BIOFLO 110 fermentor with 0.5 liter working volume to provide a controlled environment with 0.5 l working volume. The dilution rate was maintained at either 0.15/hr or 0.35/hr until it reached a steady state after 4 to 6 residence times. The temperature was controlled at 37° C. The pH was measured using a glass electrode (METTLER-TOLEDO™) and controlled at a set point of 7.0 by adding 3N $HNO_3$ or 3N NaOH. Dissolved oxygen (DO) was monitored using a polarographic oxygen electrode (METTLER-TOLEDO™) and the DO was maintained above 80% saturation by an automated controller which adjusts the agitation appropriately using a feed back control loop. The air was filtered through a 0.22-µm inline filter and delivered to the culture at a flow rate of 2.5 liters/min. The initial agitation speed was set at 500 rpm. The effluent gases were bubbled through a 1 M $CuSO_4$ solution to prevent release of bacteria. Samples were taken during the steady state phase after 4, 5 and 6 residence times.

Example 3

Aerobic Shake Flask Experiments

Since isoamyl alcohol and isoamyl acetate are volatile compounds, aerobic shake flask experiments were carried out in flasks capped with rubber stoppers. The rubber stopper facilitates headspace gas sampling for analysis of volatile compounds (isoamyl acetate and isoamyl alcohol) and also prevents their escape from the flask. For aerobic cultures, 10 ml culture medium was used in a 250 ml Erlenmeyer flask and preliminary experiments have shown that the high headspace to culture medium ratio (240:10 air-to-liquid ratio) provided sufficient aeration over the course of the experiment. The cultures were grown in an orbital shaker at the required temperature. At the end of the experiment (24 hrs), the cultures were analyzed for isoamyl acetate production.

Example 4

Quantification of Isoamyl Compounds

Isoamyl alcohol and isoamyl acetate content was determined by headspace gas chromatography. The flask or the tube, as the case may be, was heated at 50° C. for 30 minutes and 1 ml of head space gas was injected into HEWLETT-PACKARD™ 6000 series gas chromatograph equipped with an ALLTECH™ 6'×¼"×2 mm POROPAK™ QS 80/100 column. A 6% ethyl acetate solution was used as internal standard.

Example 5

Acetate Formation in an Aerobic Chemostat

Figure 4:
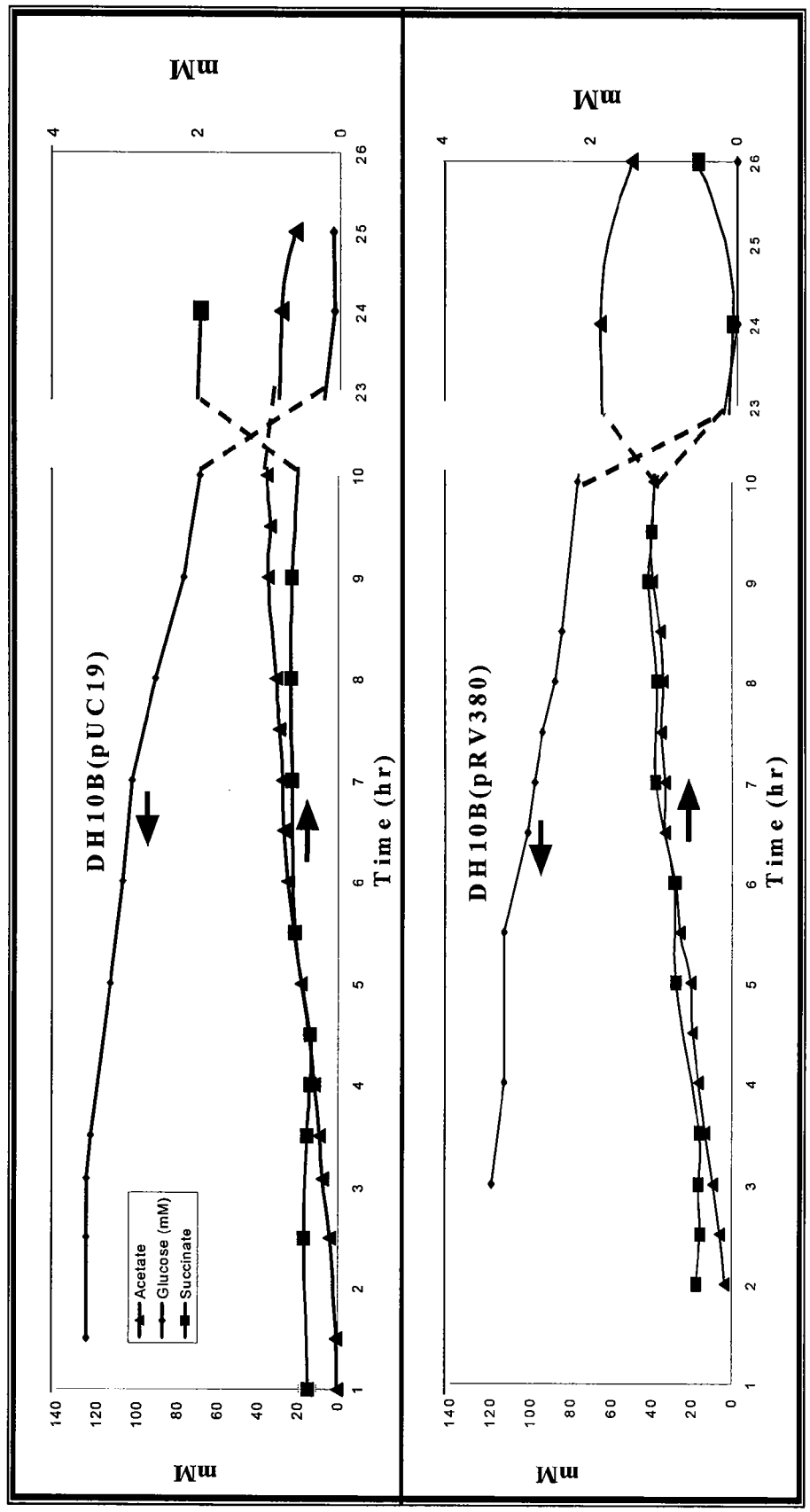
FIG. 4 illustrates metabolite concentrations of acetate, glucose and succinate in bacterial strains overexpressing pantothenate kinase.

The specific acetate production rate for the two strains DH10B(pUC19) and DH10B(pRV480) is shown in FIG. 4. The results show that the overexpression of PanK leads to an increase in acetate levels and suggests that higher carbon flux through the A-CoA node was achieved by expressing PanK. This result was confirmed by the decreased levels of succinate in the strain expressing PanK (FIG. 4).

Example 6

Overexpression of Pantothenate Kinase

The variation in CoA/A-CoA levels was studied in a batch reactor to study the overexpression of pantothenate kinase.

Figure 5:
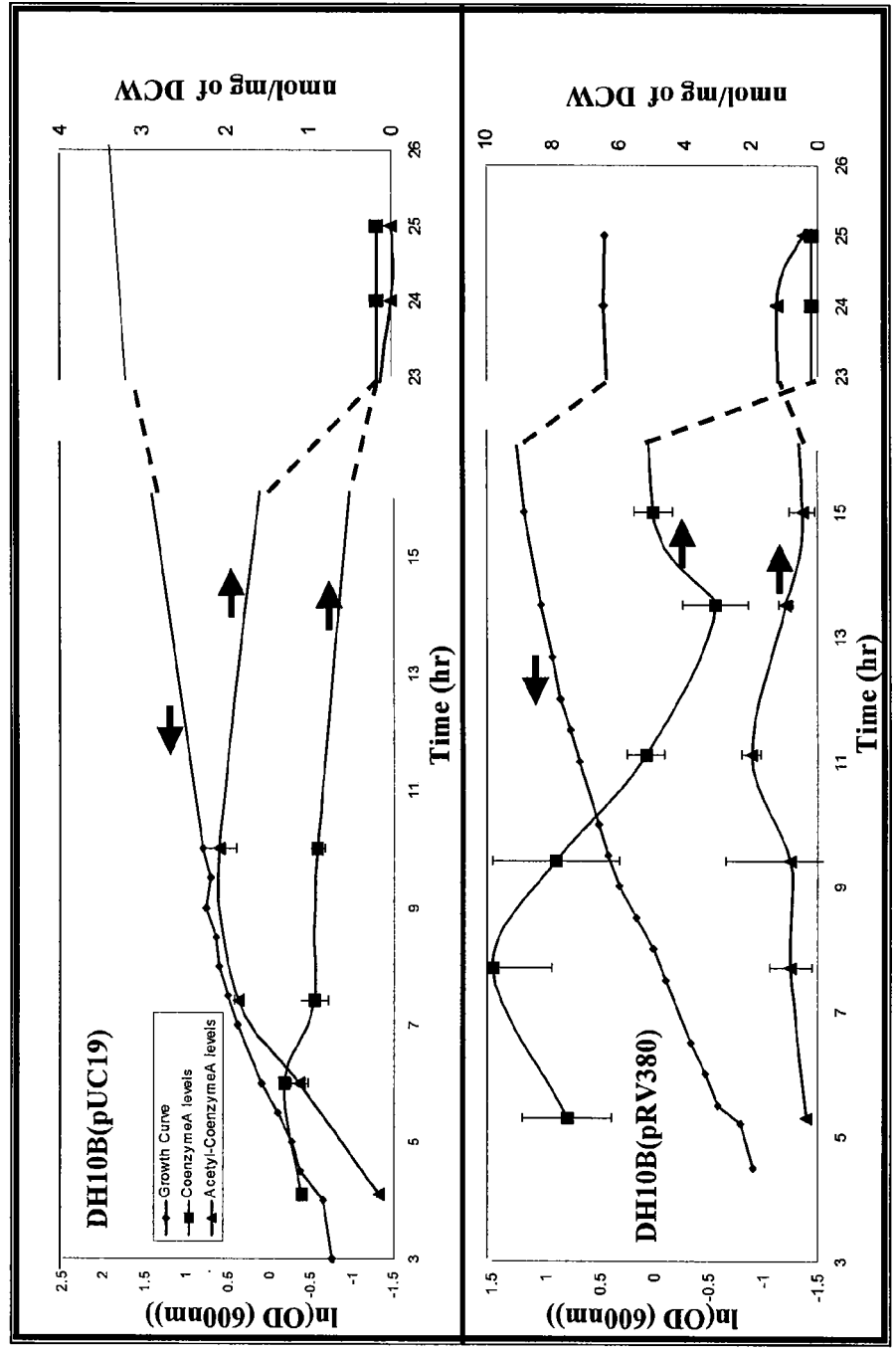
FIG. 5 illustrates intracellular CoA and A-CoA levels of steady state chemostat cultures.

The intracellular CoA/A-CoA levels were studied using the recombinant strains DH10B(pUC19) and DH10B (pRV480) in a batch reactor using M9 medium. The results show that the overexpression of PanK leads to an increase in CoA/A-CoA levels (FIG. 5). Additionally, the increase in CoA levels is greater than the observed increase in A-CoA levels.

The intracellular CoA/A-CoA levels were studied in the same two strains above in the presence of 5 mM pantothenic acid (FIG. 6a). The strain overexpressing PanK showed higher levels of intracellular A-CoA in the presence of pantothenic acid relative to the non-supplemented control experiments.

Example 7

Isoamyl Acetate Production

Figure 6:
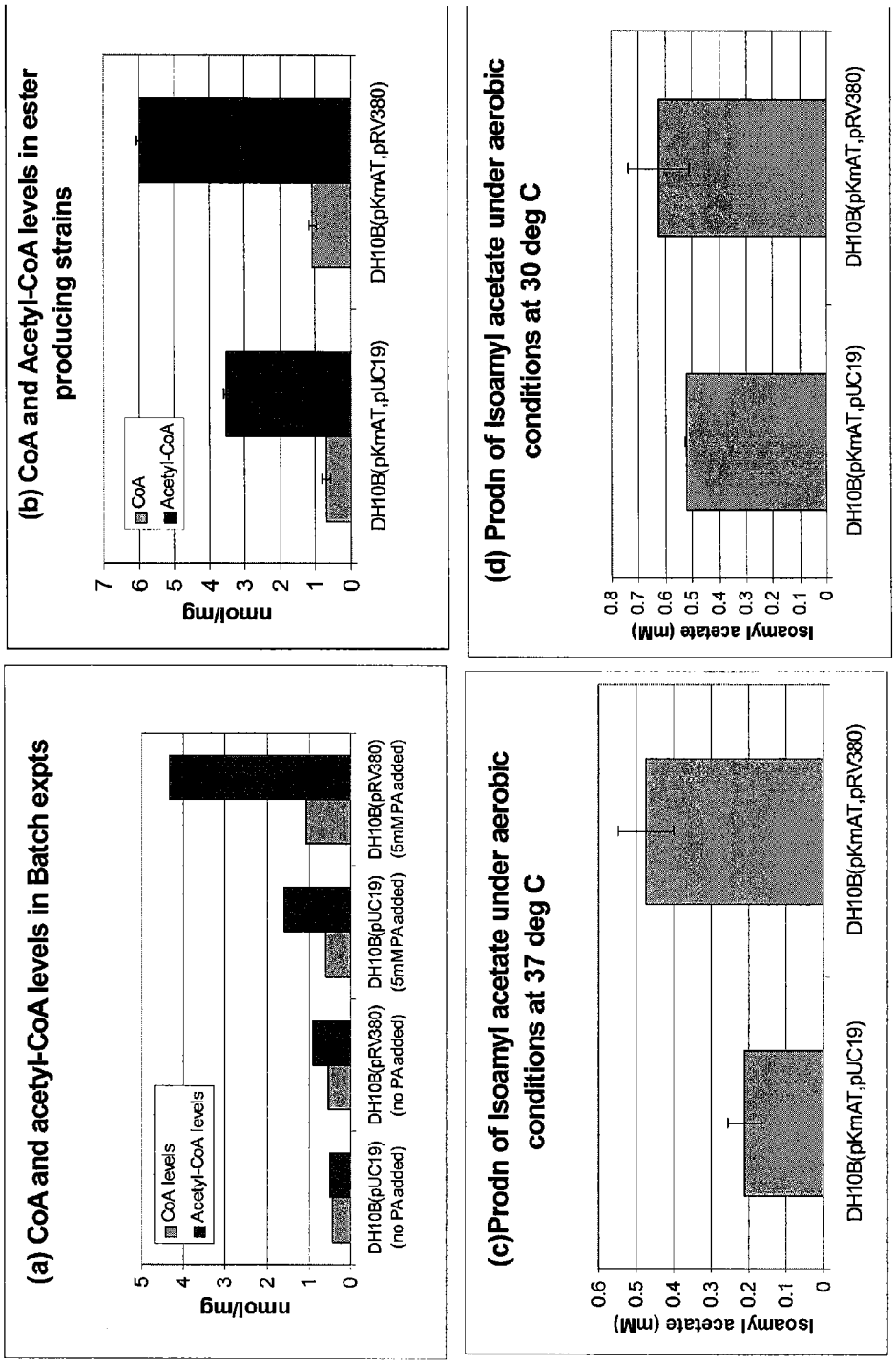
FIG. 6 illustrates intracellular CoA and A-CoA levels in bacterial strains overexpressing pantothenate kinase.

Two recombinant strains were constructed, DH10B(pKmAT, pUC19) and DH10B(pKmAT, pRV380). The latter strain overexpresses PanK and displays higher isoamyl acetate production relative to the control strain (FIG. 6).

Example 8

CoA/A-CoA Levels

Figure 7:
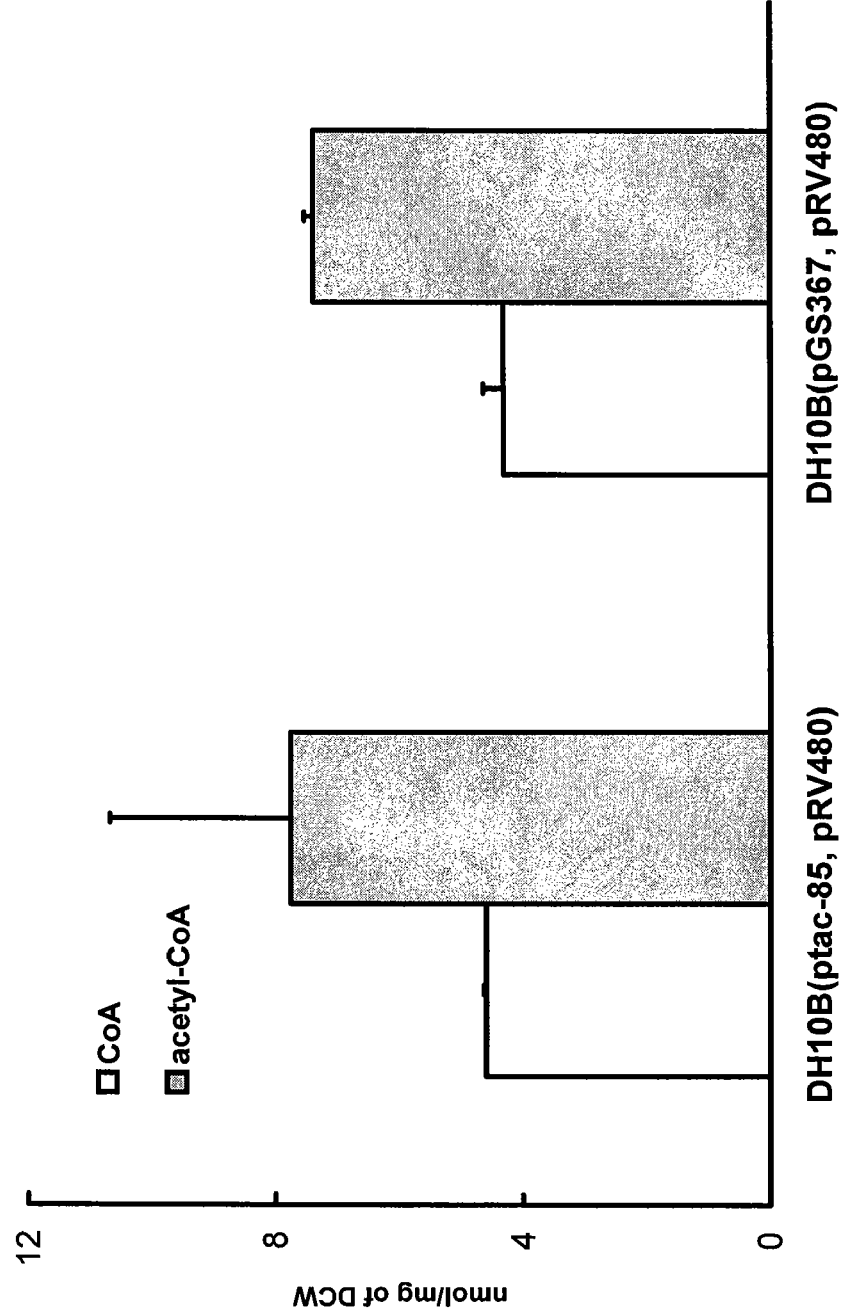
FIG. 7 illustrates levels of CoA, A-CoA and isoamyl acetate in bacterial strains overexpressing pantothenate kinase in the presence of pantothenate supplement.

The variation in CoA/A-CoA levels was studied in an aerobic chemostat to study the coexpression of pyruvate dehydrogenase and pantothenate kinase, and the results are shown in FIG. 7. The precursor compound pantothenic acid (5 mM) was supplemented in all these experiments as a substrate for the overexpressed pantothenate kinase to increase intracellular CoA/A-CoA levels.

The intracellular CoA/A-CoA levels were studied using the recombinant strains DH10B(ptac-85, pRV480) and DH10B(pGS367, pRV480) in an aerobic chemostat using Luria Broth medium at two different dilution rates (0.15/hr and 0.35/hr). Both strains overexpress pantothenate kinase and are supplemented with pantothenate in the culture medium, which enables them to have an elevated levels of intracellular CoA/A-CoA. However, only the strain DH10B (pGS367, pRV480) overexpresses pyruvate dehydrogenase whereas the strain DH10B(ptac-85, pRV480) carries a control plasmid. The intracellular levels of CoA/A-CoA are below the detection limit of HPLC (0.04 nmol) for both the strains at a dilution rate of 0.15/hr. At such a low dilution rate the *E. coli* culture at steady state corresponds more to the stationary phase of cell growth. This observation is consistent with the observation that the CoA/A-CoA levels were negligible in the stationary growth phase.

At a dilution rate of 0.35/hr, the intracellular CoA/A-CoA levels were within the detectable range of HPLC. At this higher dilution rate, the cell culture at steady state corresponds to exponential growth phase and the intracellular levels of CoA and A-CoA are significant and detectable. This is again consistent with earlier studies where high levels of CoA and A-CoA levels were observed during the exponential growth phase. However, there was no significant change in the intracellular A-CoA level with the overexpression of pyruvate dehydrogenase in addition to pantothenate kinase (FIG. 7).

Example 9

Glucose Uptake and Acetate Formation

Figure 8:
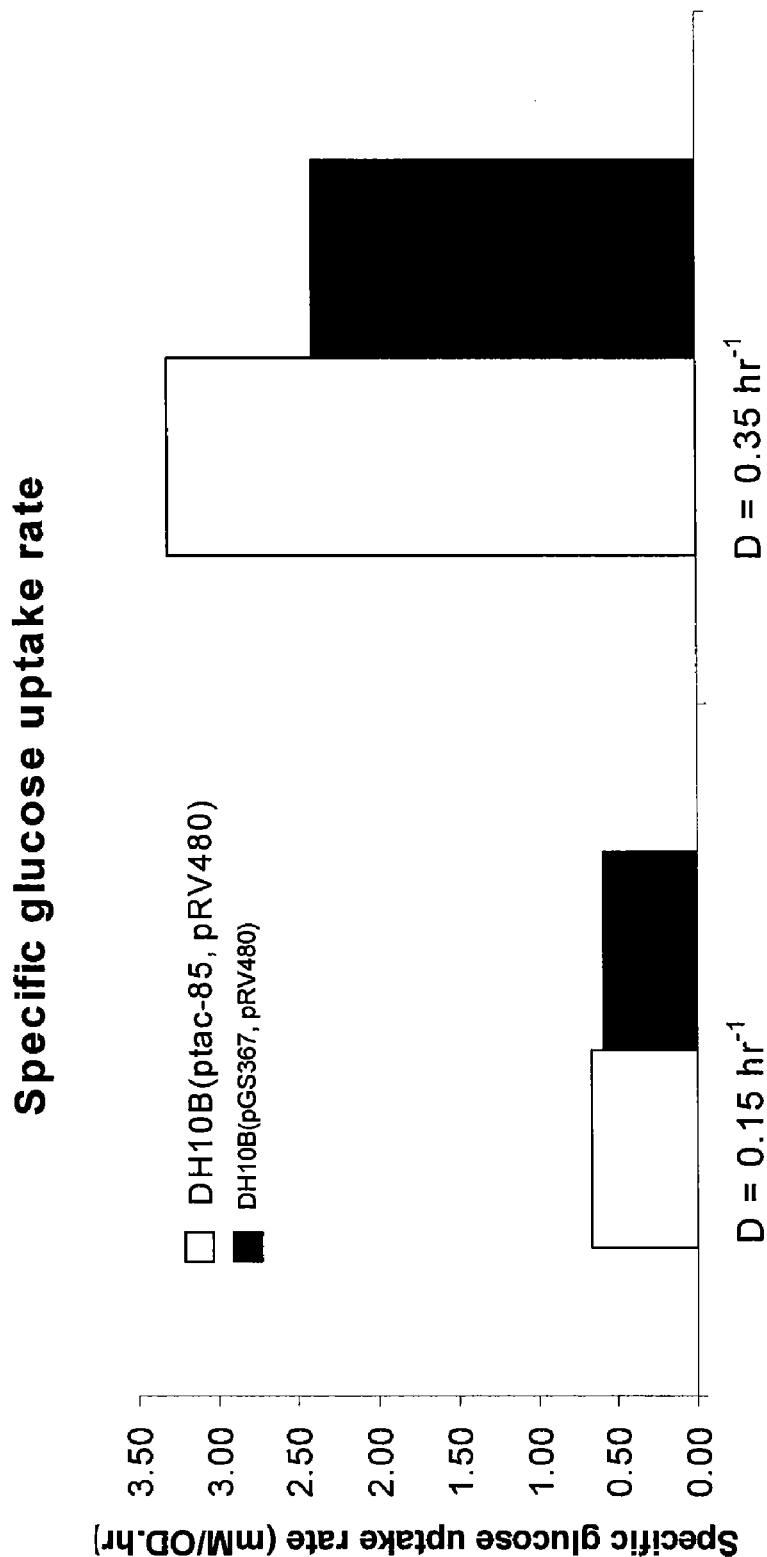
FIG. 8 illustrates the glucose uptake rate of steady state chemostat cultures.

The specific glucose uptake rate for the two strains DH10B (ptac-85, pRV480) and DH10B(pGS367, pRV480) at two different dilution rates is shown in FIG. 8. Both strains showed higher glucose uptake rate at the higher dilution rates. At a dilution rate of 0.35/hr, the control strain DH10B(ptac-85, pRV480), exhibited a significantly higher uptake rate than DH10B(pGS367, pRV480), which overexpresses both PanK and PDH.

Figure 9:
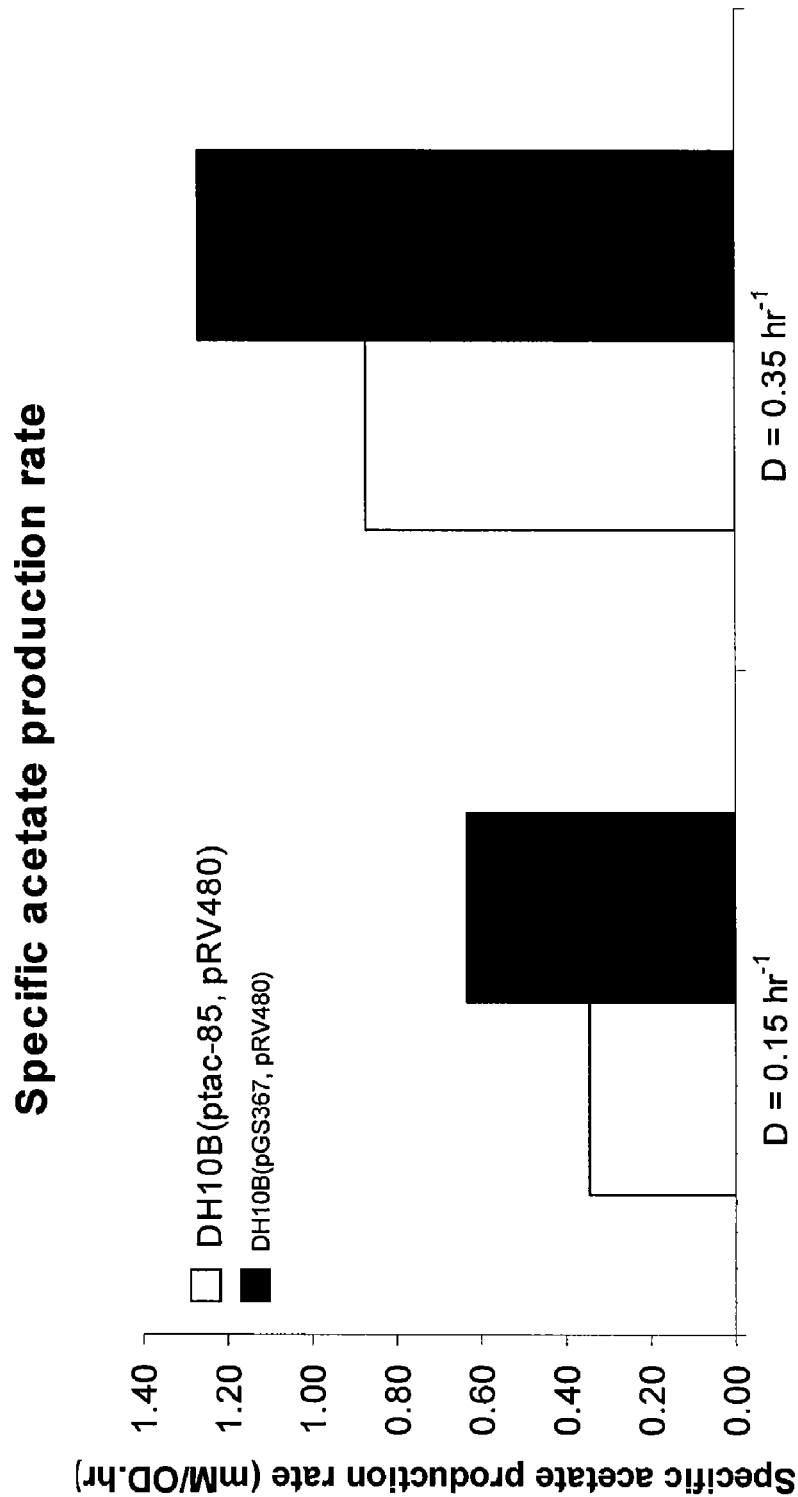
FIG. 9 illustrates the acetate production rate of steady state chemostat cultures.

The specific acetate production rate for DH10B(pGS367, pRV480) is significantly higher than the control strain at both dilution rates (FIG. 9). At the dilution rate of 0.15/hour, DH10B(pGS367, pRV480) displays a 103% increase in acetate production. At a dilution rate of 0.35/hour, DH10B (pGS367, pRV480) displays a 53% increase in acetate production. These results suggested that higher carbon flux through the A-CoA node was achieved by co-expressing both PanK and PDH.

Example 10

Coexpression of PDH and PANK

Two recombinant strains were constructed, DH10B(ptac-85, pATCA) and DH10B(pGS367, pATCA). Both strains overexpress pantothenate kinase due to which both strains have elevated CoA/A-CoA levels when the cell culture medium is supplemented with pantothenate. Similarly both the strains overexpress alcohol acetyltransferase and therefore can produce isoamyl acetate when isoamyl alcohol is added externally to the cell culture medium. However, only the strain DH10B(pGS367, pATCA) overexpresses PDH thereby enhancing the carbon flux from pyruvate to A-CoA in this strain. The production of isoamyl acetate was studied in both strains to elucidate the effect of this coexpression on isoamyl acetate production. No increase in isoamyl acetate production was observed upon overexpression of pyruvate dehydrogenase in addition to pantothenate kinase (data not shown).

The results of isoamyl acetate production can be explained if the competition of acetate production pathway at the A-CoA node is taken into consideration. The enzyme alcohol acetyltransferase (AAT), which condenses isoamyl alcohol and A-CoA to form isoamyl acetate, might be competing less effectively with phosphotransacetylase for the common substrate A-CoA. Phosphotransacetylase (PTA) catalyses the formation of acetyl phosphate from A-CoA, the first step in the formation of acetate. The PTA enzyme has greater affinity towards A-CoA when compared to AAT. This observation suggests that the acetate production pathway might be stronger than the ester production pathway and possibly drains the enhanced carbon flux.

Example 11

Channeling the Enhanced Carbon Flux to Isoamyl Acetate Production

Since the acetate production pathway is more competitive than the isoamyl acetate production pathway at the A-CoA node, it was hypothesized that with the inactivation of acetate production pathway, the carbon flux could be more efficiently channeled to ester production. Under such conditions the enhanced carbon flux through the A-CoA node can have a beneficial effect on ester production. To test this hypothesis, a ackA-pta deletion mutant (a strain containing mutant copies acetate kinase (ackA) and phosphoacetyltransferase (pta)) YBS121 was used to construct two recombinant strains, YBS121(ptac-85, pATCA) and YBS121(pGS367, pATCA).

Figure 10:
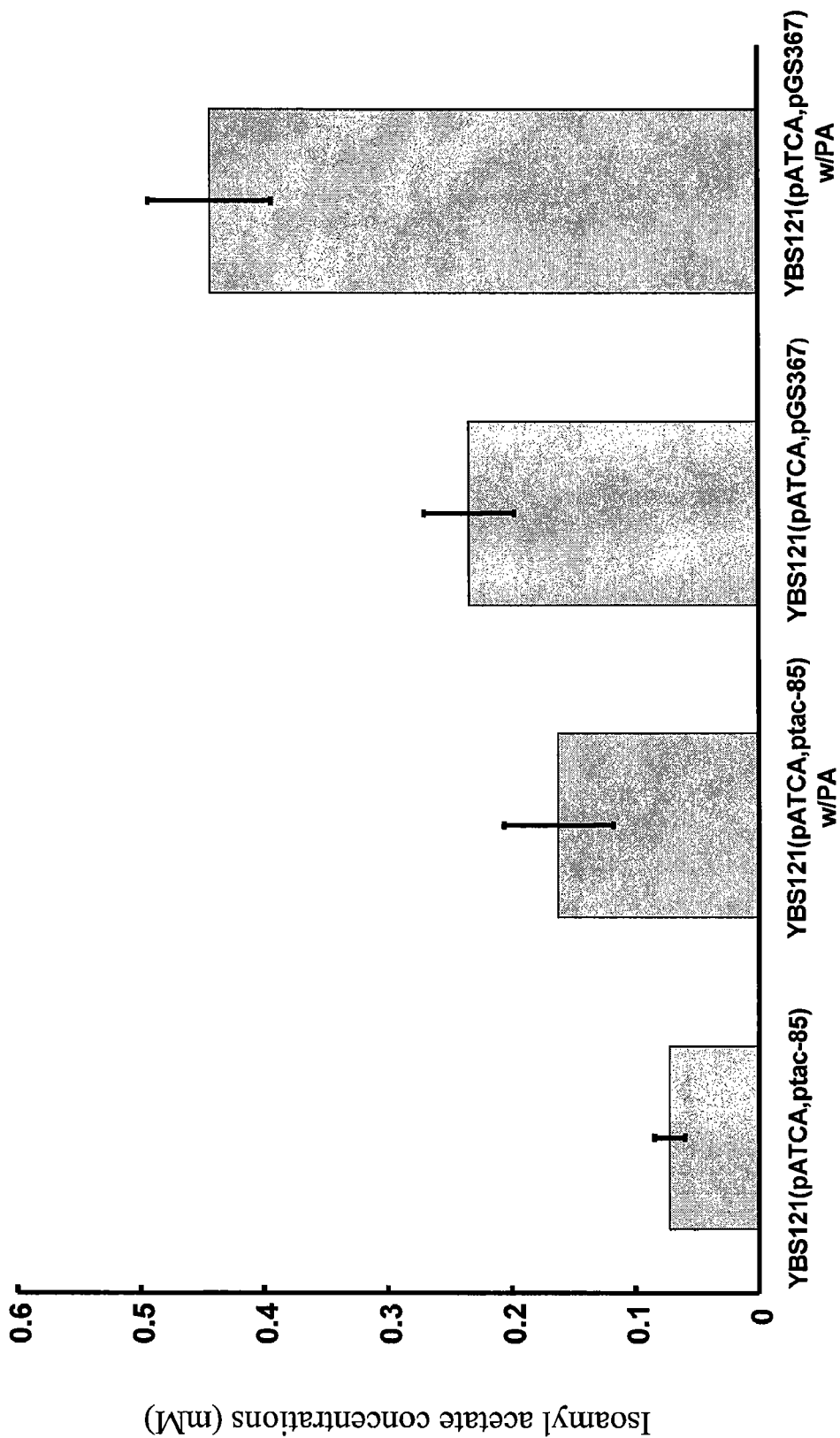
FIG. 10 illustrates isoamyl acetate concentrations in the strains tested.

The supplementation of pantothenic acid is necessary in addition to overexpression of pantothenate kinase to increase intracellular CoA/A-CoA levels. This supplementation/non-supplementation of pantothenic acid to the culture medium was used as control parameter to maintain intracellular CoA/A-CoA levels at elevated/basal levels. A series of triplicate experiments were performed to study the effect of CoA/A-CoA manipulation and PDH overexpression on isoamyl acetate production both individually and in combination. Even though the plasmid pATCA, overexpresses PanK, the supplementation of the precursor pantothenic acid is required to increase CoA/A-CoA levels. The results of these experiments are shown in FIG. 10.

The strain YBS121(ptac-85, pATCA) produced 0.07 mM isoamyl acetate without supplementation of pantothenic acid. Upon supplementation of pantothenic acid, the isoamyl acetate production in the same strain increased to 0.16 mM, a 225% increase. These results indicate that the CoA/A-CoA manipulation leads to a 124% increase in isoamyl acetate production. However, the strain YBS121(pGS367, pATCA) produced 0.23 mM isoamyl acetate without supplementation of pantothenic acid, which is a 223% increase compared to the control strain YBS121(ptac-85, pATCA) (no pantothenic acid addition). This result shows that overexpression of pyruvate dehydrogenase is more efficient in increasing isoamyl acetate production compared to CoA/A-CoA manipulation. However the same strain (YBS121(pGS367, pATCA)) produced 0.44 mM of isoamyl acetate upon supplementation of pantothenic acid. The increase in isoamyl acetate production is about 5-fold, upon simultaneous manipulation of CoA/A-CoA levels and enhancing carbon flux from pyruvate node. This significant increase in isoamyl acetate production illustrate that the strategies of cofactor manipulation and carbon flux enhancement are synergistic and much more effective in increasing isoamyl acetate production, than using either of the strategies alone.

Example 12

Effect of PDH and PANK Coexpression

Figure 11:
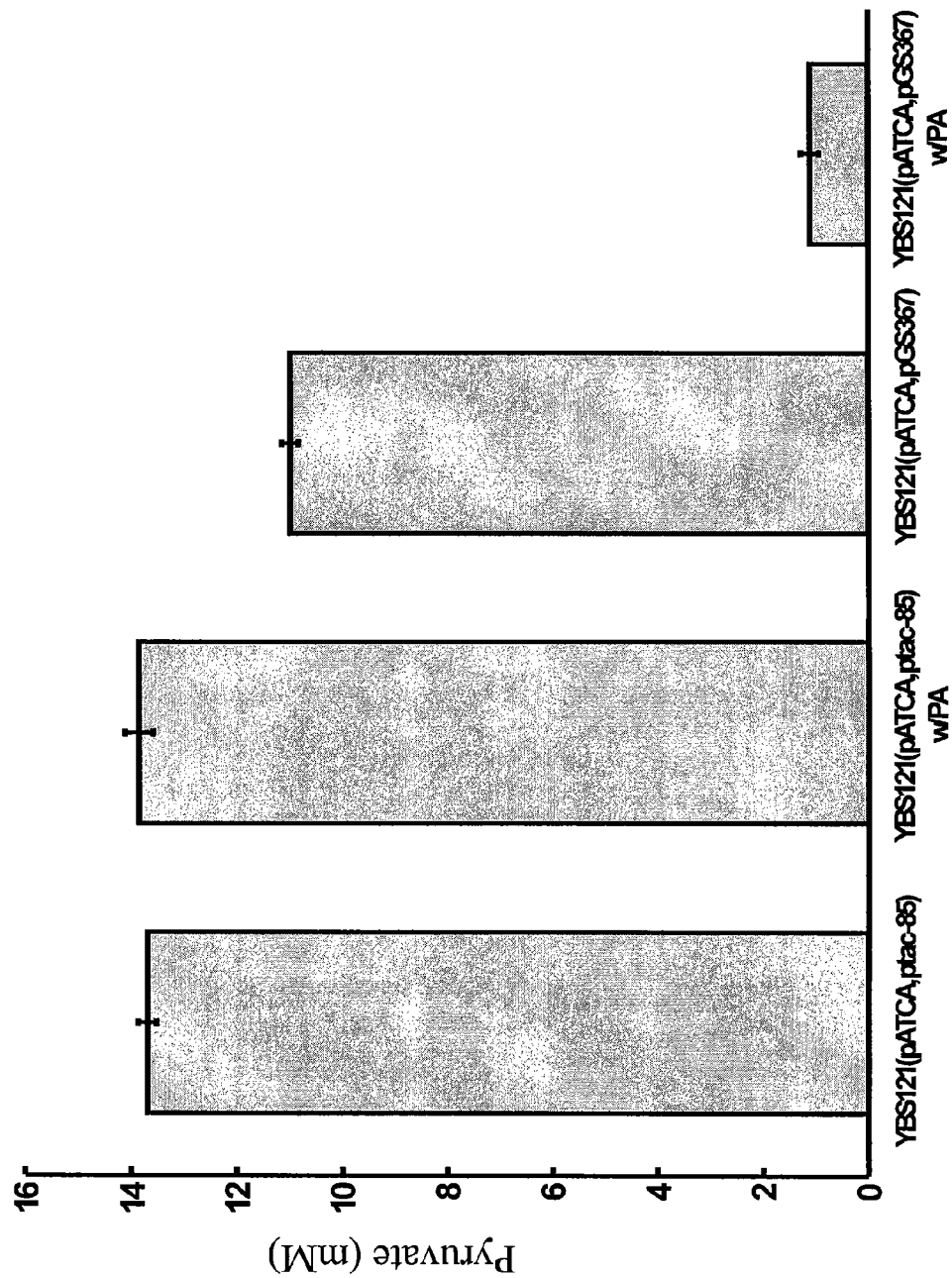
FIG. 11 illustrates pyruvic acid concentrations in the strains tested.

When the above experiments are repeated without any supplementation of pantothenic acid, notable differences were observed in the accumulation of pyruvate and the results are as shown in FIG. 11. The ackA-pta mutation relieves the highly competitive phosphotransacetylase enzymatic step of the acetate formation pathway and makes A-CoA more accessible to alcohol acetyltransferase. However, the inactivation of the acetate formation pathway leads to metabolic imbalance at the pyruvate node. The carbon flux is bottled up at the pyruvate node leading to excretion of pyruvate to the extracellular medium. The recombinant strain, YBS121(ptac-85, pATCA), an acetate pathway deletion mutant strain, produced 13.69 mM of pyruvate as expected. Increasing intracellular CoA/A-CoA levels increases this excretion slightly. When the intracellular CoA/A-CoA levels were increased in the strain YBS121(ptac-85, pATCA) upon pantothenic acid supplementation, it produced 13.81 mM of pyruvate. Overexpression of pyruvate dehydrogenase could convert some of this excess pyruvate to A-CoA leading to a decrease in pyruvate excretion. The strain YBS121(pGS367, pATCA), which overexpresses pyruvate dehydrogenase produced only 10.97 mM of pyruvate. This overexpression of pyruvate dehydrogenase lead to a 21% decrease in pyruvate accumulation. However, a significant amount of pyruvate is still excreted even in this case. The same strain YBS121(pGS367, pATCA) when supplemented with pantothenic acid, produced only 1.1 mM of pyruvate, which is a significant drop in pyruvate excretion, when compared to the control strain YBS121(ptac-85, pATCA). When the overexpression of pyruvate dehydrogenase is accompanied by an increase in availability of CoA, most of the excess pyruvate could be efficiently converted to A-CoA. The coexpression of pyruvate dehydrogenase and pantothenate kinase relieved the metabolic imbalance at pyruvate node and the pyruvate excretion dropped to negligible levels. This metabolic engineering strategy efficiently channels the excess carbon flux from pyruvate node to A-CoA node in an acetate pathway deletion mutant. The drop in pyruvate excretion leads to a more efficient utilization of the carbon source without any loss at the pyruvate node.

3. The bacterium of claim 1, where the panK gene is under the control of the lac promoter and the atf gene is under the control of the ptb promoter.

4. The bacterium of claim 1, wherein said bacterium produces increased acetic ester when grown in culture supplemented with pantothenate, as compared to a control bacterium without said panK, pdh, and atf genes.

5. The bacterium of claim 1, wherein said bacterium produces increased isoamyl acetate when grown in culture supplemented with pantothenate, as compared to a control bacterium without said panK, pdh, and atf genes.

6. The bacterium of claim 2, where the panK gene is under the control of the lac promoter and the atf gene is under the control of the ptb promoter.

7. The bacterium of claim 2, wherein said bacterium produces increased acetic ester when grown in culture supplemented with pantothenate, as compared to a control bacterium without said panK, pdh, and atf genes.

8. The bacterium of claim 2, wherein said bacterium produces increased isoamyl acetate ester when grown in culture supplemented with pantothenate, as compared to a control bacterium without said panK, pdh, and atf genes.

What is claimed is:

1. A bacterium comprising a recombinant bacterial panK gene overexpressing pantothenate kinase (PANK), a recombinant bacterial pdh gene overexpressing pyruvate dehydrogenase (PDH), and a recombinant yeast atf gene overexpressing alcohol acetyl transferase (ATF),
   a) wherein said bacteria has more PANK, PDH and ATF activity than a bacteria without said recombinant panK, pdh, or atf genes,
   b) wherein said bacterium produces increased flux through the Acetyl-CoA node when grown in culture supplemented with pantothenate.

2. The bacterium of claim 1, further comprising a mutant ackA gene and a mutant pta gene, such that said bacterium produces less acetate kinase activity and less phosphoacetyltransferase activity, as compared to said bacterium without said mutant ackA and pta genes.

9. An E. coli comprising:

a) one or more expression vectors that overexpresses wild type E. coli pantothenate kinase (PANK), E. coli pyruvate dehydrogenase (PDH), and yeast alcohol acetyl transferase (ATF), as compared with a bacteria that lacks said one or more expression vectors; and b) deletions in both the ackA gene and the pta gene;
wherein said E. coli produces increased flux through the Acetyl-CoA node when grown in culture supplemented with pantothenate, as compared with said E. coli without said expression vectors or said deletions.

* * * * *

UNITED STATES PATENT AND TRADEMARK OFFICE
CERTIFICATE OF CORRECTION

PATENT NO. : 7,901,924 B2
APPLICATION NO. : 12/340349
DATED : March 8, 2011
INVENTOR(S) : Ka-Yiu San, George Nelson Bennett and Ravishankar V. Vadali It is certified that error appears in the above-identified patent and that said Letters Patent is hereby corrected as shown below:

IN THE SPECIFICATIONS:

Column 1, Line 15 under subtitle "FEDERALLY SPONSORED RESEARCH STATEMENT" please substitute with the following paragraph:

> This invention was made with government support under Grant Nos. BES-0118815 and 0000303 by the United States Government and the National Science Foundation. The government has certain rights in the invention.

IN THE CLAIMS:

In claims 1 through 9, certain terms should be italicized

1. A bacterium comprising a recombinant bacterial *panK* gene overexpressing pantothenate kinase (PANK), a recombinant bacterial *pdh* gene overexpressing pyruvate dehydrogenase (PDH), and a recombinant yeast *atf* gene overexpressing alcohol acetyl transferase (ATF),
   a) wherein said bacteria has more PANK, PDH and ATF activity than a bacteria without said recombinant *panK*, *pdh*, or *atf* genes,
   b) wherein said bacterium produces increased flux through the Acetyl-CoA node when grown in culture supplemented with pantothenate.

2. The bacterium of claim 1, further comprising a mutant *ackA* gene and a mutant *pta* gene, such that said bacterium produces less acetate kinase activity and less phosphoacetyltransferase activity, as compared to said bacterium without said mutant *ackA* and *pta* genes.

3. The bacterium of claim 1, where the *panK* gene is under the control of the lac promoter and the *atf* gene is under the control of the *ptb* promoter.

Signed and Sealed this
Twenty-first Day of June, 2011

David J. Kappos
*Director of the United States Patent and Trademark Office*

(continued)

4. The bacterium of claim 1, wherein said bacterium produces increased acetic ester when grown in culture supplemented with pantothenate, as compared to a control bacterium without said *panK*, *pdh*, and *atf* genes.

5. The bacterium of claim 1, wherein said bacterium produces increased isoamyl acetate when grown in culture supplemented with pantothenate, as compared to a control bacterium without said *panK*, *pdh*, and *atf* genes.

6. The bacterium of claim 2, where the *panK* gene is under the control of the *lac* promoter and the *atf* gene is under the control of the *ptb* promoter.

7. The bacterium of claim 2, wherein said bacterium produces increased acetic ester when grown in culture supplemented with pantothenate, as compared to a control bacterium without said *panK*, *pdh*, and *atf* genes.

8. The bacterium of claim 2, wherein said bacterium produces increased isoamyl acetate ester when grown in culture supplemented with pantothenate, as compared to a control bacterium without said *panK*, *pdh*, and *atf* genes.

9. An *E. coli* comprising:

a) one or more expression vectors that overexpresses wild type *E. coli* pantothenate kinase (PANK), *E. coli* pyruvate dehydrogenase (PDH), and yeast alcohol acetyl transferase (ATF), as compared with a bacteria that lacks said one or more expression vectors; and b) deletions in both the *ackA* gene and the *pta* gene;
wherein said *E. coli* produces increased flux through the Acetyl-CoA node when grown in culture supplemented with pantothenate, as compared with said *E. coli* without said expression vectors or said deletions.